(12) United States Patent
Fuchs (10) Patent No.: US 10,646,655 B2
(45) Date of Patent: May 12, 2020

(54) SYRINGE

(71) Applicant: F+K Innovationen GmbH & Co. KG, Baden-Baden (DE)

(72) Inventor: Karl-Heinz Fuchs, Radolfzell (DE)

(73) Assignee: F+K Innovationen GmbH & Co. KG, Baden-Baden (DE)

( * ) Notice: Subject to any disclaimer, the term of this patent is extended or adjusted under 35 U.S.C. 154(b) by 111 days.

(21) Appl. No.: 15/748,752

(22) PCT Filed: Jul. 28, 2016

(86) PCT No.: PCT/EP2016/068088
§ 371 (c)(1),
(2) Date: Jan. 30, 2018

(87) PCT Pub. No.: WO2017/017229
PCT Pub. Date: Feb. 2, 2017

(65) Prior Publication Data
US 2019/0022321 A1 Jan. 24, 2019

(30) Foreign Application Priority Data

Jul. 30, 2015 (DE) .......................... 10 2015 112 564

(51) Int. Cl.
*A61M 5/24* (2006.01)
*A61M 5/20* (2006.01)
(Continued)

(52) U.S. Cl.
CPC ............ *A61M 5/24* (2013.01); *A61M 5/2033* (2013.01); *A61M 5/31551* (2013.01);
(Continued)

(58) Field of Classification Search
CPC .. A61M 5/24; A61M 5/2033; A61M 5/31551; A61M 5/31563; A61M 5/326;
(Continued)

(56) References Cited

U.S. PATENT DOCUMENTS

| | | | | |
|---|---|---|---|---|
| 5,017,191 A | * | 5/1991 | Yamada | A61M 5/28 604/243 |
| 2010/0036326 A1 | * | 2/2010 | Matusch | A61M 5/30 604/198 |

(Continued)

FOREIGN PATENT DOCUMENTS

WO 2013064676 A1 5/2013

OTHER PUBLICATIONS

International search report for patent application PCT/EP2016/068088 dated Nov. 17, 2016.

*Primary Examiner* — Nathan R Price
*Assistant Examiner* — Dung T Ulsh
(74) *Attorney, Agent, or Firm* — Bachman & LaPointe, PC (57) ABSTRACT

A syringe having a dispensing element (20) and having a mounting element (2), wherein the dispensing element (20) has a dispensing sleeve (21) and a leaf spring system (3), wherein the mounting element (2) has a syringe body (17), and an injection needle (16) is formed on one end on the syringe body (17) and a detent-engagement flange (19) is formed on the other end, wherein, in the syringe body (17), there is arranged a movable stopper (18), wherein the leaf spring system (3) comprises a piston (6) and a spiral spring (5) arranged around the piston (6), wherein the piston (6) can be slid into the dispensing sleeve (21), and the spiral spring (6) is arranged between a leaf spring base (22) and a spiral spring abutment, wherein the piston (6) abuts against the stopper (18), wherein the dispensing sleeve (21) has a guide duct and the dispensing sleeve (21) comprises a first locking means (7) and a second locking means (9), wherein the detent-engagement flange (19) is movable in the guide duct and is fixable and releasable at the first locking means (7) or the second locking means (9).

8 Claims, 7 Drawing Sheets

(51) Int. Cl.
    *A61M 5/315*     (2006.01)
    *A61M 5/32*     (2006.01)
    *A61M 5/46*     (2006.01)
    *A61M 5/28*     (2006.01)

(52) U.S. Cl.
    CPC ........ *A61M 5/31563* (2013.01); *A61M 5/326* (2013.01); *A61M 5/3287* (2013.01); *A61M 5/46* (2013.01); *A61M 5/28* (2013.01); *A61M 5/31581* (2013.01); *A61M 2005/206* (2013.01); *A61M 2005/208* (2013.01); *A61M 2005/2013* (2013.01); *A61M 2005/244* (2013.01); *A61M 2005/2411* (2013.01)

(58) Field of Classification Search
    CPC ........ A61M 5/3287; A61M 5/46; A61M 5/28; A61M 5/31581; A61M 2005/2013; A61M 5/206; A61M 5/208; A61M 5/2411; A61M 5/244
    See application file for complete search history.

(56) References Cited

U.S. PATENT DOCUMENTS

| | | | |
|---|---|---|---|
| 2012/0074001 A1* | 3/2012 | Genosar | A61J 1/2089 206/219 |
| 2012/0220954 A1* | 8/2012 | Cowe | A61M 5/2033 604/228 |
| 2014/0005609 A1 | 1/2014 | Ina | |
| 2017/0106146 A1* | 4/2017 | Folk | A61M 5/20 |

\* cited by examiner

SYRINGE

TECHNICAL FIELD

The invention relates to a syringe.

PRIOR ART

Various disposable syringes are known from the prior art, but they require the use of a great deal of material and accordingly generate a lot of waste. The known disposable syringes are discarded in their entirety after use but are in principle still usable, i.e. the syringes can be filled again, which in turn has the disadvantage that they are improperly used on the drugs scene, which increases the risk of infectious diseases transmissible via the blood stream.

OBJECT OF THE INVENTION

The object of the invention is to make available a disposable syringe which substantially avoids the disadvantages of the prior art and has a user-friendly structure posing low risk of injury in a system independent use.

Achieving the Object

The object is achieved by the features disclosed herein.

The syringe according to the invention is a syringe construction by which all media that can be introduced via a syringe can be introduced into the human body. In an illustrative embodiment according to the invention, it is a disposable syringe, wherein it is not the entire construction that can be used just once. A discharge element is designed in such a way that it is reusable. The discharge element serves for the use of a syringe body, which can be actuated by the discharge element. After the single actuation, the syringe body is intended to be discarded.

WO 2013/064676 was an application for a system which meets the requirements as regards sustainability and misuse on the drugs scene and material wastage. The new application is based on this application and is intended to eliminate the risk of injury by the needle and to guarantee a degree of user independence and automation.

The syringe according to the invention is composed of the discharge element and the storage element. The discharge element is a manual instrument that is produced substantially in one piece from plastic.

The discharge element is composed primarily of a discharge sleeve and of a leaf spring system. The leaf spring system is composed of a leaf spring base and a ceiling region. The ceiling region has a discharge sleeve, wherein the discharge sleeve extends away from the ceiling region at the other end of the side facing toward the leaf spring base.

Moreover, the leaf spring base comprises a plunger, wherein the plunger extends from the leaf spring base to the ceiling region and is displaceable into the discharge sleeve. The displaceability of the plunger into the discharge sleeve is achieved by the fact that, between the leaf spring base and the ceiling region, a compression spring element is formed integrally with the leaf spring base and the ceiling region. The compression spring element entails compressible spring elements which are integrally connected to the the ceiling region and the leaf spring base. The number of the compression spring elements is dependent on the individual case. In a preferred illustrative embodiment, three to four compression spring elements extend at one end and the other end, respectively, from the leaf spring base to the ceiling region, such that a closed structure is obtained in which the plunger extends centrally from the leaf spring base to the ceiling region.

The leaf spring system comprises a plunger and a spiral spring arranged around the plunger, wherein the plunger and the spiral spring can be pushed into the discharge sleeve and the spiral spring is arranged between the leaf spring base and a spiral spring stop of the storage element, wherein the plunger abuts against the stopper, but the spiral spring abuts against the spiral spring stop. The spiral spring stop is part of the storage element of the. When the storage element is pushed into the discharge sleeve, the spiral spring is compressed. To ensure that the compression spring element is not unintentionally pressed apart, the compression spring element comprises a retention element. The latter is, for example, a foil which is arranged in the compression spring element in such a way that, when the storage element is inserted into the discharge sleeve, the compression spring element can be expanded only into a defined position. The stopper is displaceable in the storage element and sealed off.

The storage element has a syringe body. An active substance is introduced in a liquid aggregate state into the syringe body. The syringe body has at one end an injection needle and at the other end an engagement flange. In addition, a movable stopper is arranged in the syringe body and forces the active substance from the injection needle upon actuation by the plunger.

The discharge sleeve has a guide channel and a puncture abutment face, wherein the puncture abutment face is arranged at the other end of the ceiling region and comprises a receptacle for a bellows. The bellows is connected to or formed integrally with the receptacle. The bellows engages around the injection needle during the use of the syringe according to the invention. Here, use means extends from the insertion of the storage element into the discharge sleeve through the puncturing of the patient's skin by the injection needle and the dispensing of the active substance through to the release of the storage element from the discharge element. An advantage of the bellows is that it offers protection against injury during the entire use. An advantage of the receptacle is that, in addition to receiving the bellows, it additionally stabilizes the discharge sleeve too.

According to the invention, the discharge element has a first locking means. The first locking means serves to lock serves to secure the storage element in the discharge element in a first position. The engagement flange of the storage element slides along in a guide channel until it is independently locked in the first position by the first locking element. The first locking element can have slide surfaces which permit the sliding along the locking element but prevent sliding back in the direction of the receptacle. In the first position, the plunger, in a defined position with correspondingly defined compression of the spiral spring, strikes against the stopper of the syringe body.

After the manual unlocking, the storage element in the discharge sleeve slides proximally as far as the body to be treated and is secured by the second locking element. The second locking element can have slide surfaces which permit the sliding along and passing of the second locking element but prevent sliding back in the direction of the receptacle.

When the storage element is secured on the second locking means, the second position is reached. In the second position, the injection needle protrudes by the desired length from the discharge sleeve. It can be enclosed either completely or only partially by the bellows. The sliding of the storage element from the first position to the second position in the direction of the puncture abutment face is achieved by the tensioned spiral spring, wherein the spiral spring partially relaxes. In the second position, the user can actuate the plunger simply by compressing the compression spring element, which forces the active substance out of the syringe body. After use, the user can release the second locking means and the spiral spring presses the used storage element automatically out of the discharge sleeve, such that the user can advantageously and easily dispose of the storage element.

The guide channel extends substantially over the entire length of the discharge sleeve. The guide channel can be designed in such a way that the discharge sleeve is a closed tube structure or is laterally open or slit.

The discharge sleeve can also have a further guide channel, wherein a further engagement flange can also be operatively connected to the further guide channel. This means, for example, that the further guide channel is arranged at 180° to the first guide channel and the storage element has a further engagement flange which is arranged at 180° to the first engagement flange.

Provision can be made here that the first locking means locks and releases the engagement flange and that the second locking means locks and releases the further engagement flange.

Moreover, the first locking means can comprise a first spring element, wherein the first spring element is integrally connected to the leaf spring system. This advantageously has the effect that the first locking means yields upon sliding past of the engagement flange and, upon release, the same spring element allows the user simple use.

In the same way, the second locking means can comprise a second spring element, wherein the second spring element is likewise integrally connected to the leaf spring system.

The disposable syringe is constructed substantially in two parts, i.e. it has a storage element as syringe body and a discharge element as adapter.

The two parts are coupled separably to each other, wherein the coupling is configured such that the emptied storage element is detachable from the discharge element, and the discharge element, being reusable, can be used again with a filled storage element.

The content of the storage element plays a secondary role in this context.

It is also conceivable that the storage element and the syringe body is produced from different materials such as plastic or glass.

Handling of the System

When equipping the discharge element with the storage element, the injection system is pretensioned via a spiral spring. When the injection system is placed onto the desired region of skin, the puncture path is limited by the puncture abutment. The system can be handled in self-medication or by the physician, since the grip faces have been integrated for both variants. Through the horizontal displacement and therefore unlocking of the system by the user, the vertical spring element frees the syringe body, such that it is moved to its position by the pretensioned spiral spring and generates the puncture in the skin. The user will subsequently actuate the injection system via the grip faces and thereby trigger the injection. After the injection, the needle with the syringe body is discarded from the system by the ejector.

The storage element is a non-refillable single-use container which cannot be filled again without being destroyed.

The storage element or the syringe body is composed of the glass or plastic body with a movable stopper without actuating plunger at the distal end and an injection needle at the proximal end, which is protected by a protective cap against causing injury.

In order to reduce the risk of injury when manually fitting the discharge element, the storage element is pressed over the injection protection cap until it engages in the discharge element. In this state, the injection needle lies damage-free inside the discharge element and the puncture abutment.

After the protective cap has been removed and the injection procedure has been triggered manually via the pretensioned spring, the storage element is displaced in its position such that the injection needle can puncture as far as the puncture abutment and the injection can be performed by the actuation of the plunger via the two plastic leaf springs.

The illustrative embodiment of the disposable syringe according to the invention is arranged in such a way that the plunger of the discharge element interacts with the stopper of the storage element, syringe body, the plunger engages in the storage element and moves the stopper in the direction of the needle. The plunger is formed in one piece with the two spring elements, wherein the spring elements the plunger is reset by its attachment to the discharge element.

A further particularity of the discharge element is the spiral spring around the plunger, which spiral spring is pretensioned upon insertion of the syringe body or of the storage element by the puncture excursion. Upon manual triggering, the retaining cam is displaced horizontally toward a spring element, such that the syringe body is displaced as far as the removal cam. After the injection, the removal cam is likewise manually moved horizontally, such that the storage element can be withdrawn from the discharge element via the protective cap.

A further particularity of the discharge element is that all two locking and unlocking cams and manually movable tabs and the plastic spring element with plunger and storage element holder are formed in one piece as a plastic part.

The disposable syringe according to the invention has three or four grip faces as actuating faces, which are each arranged at the end of the force expansion direction of the spring element and permits handling for the physician or in self-medication and are likewise formed in one piece with the spring element.

This has the advantageous effect that the plunger is pushed into the storage element by three fingers which bear on the actuating faces and which are pressed counter to the force of the spring element. When the grip with the fingers is released, the spring element restores the actuating faces to the starting position.

The user independence is achieved through the automated sequence of the injection in conjunction with the manual triggering and unlocking with a high degree of safety and reduction of injuries by the injection needle.

In one illustrative embodiment, the discharge element has an unlocking variant. Here, an unlocking element is mounted on the grip in an upper region. The upper region is the region of the grip which is directed toward the syringe body. A vertical unlocking means is connected to the spring element in the region of the grip face. This concerns the first manual unlocking of the system for the injection.

The second unlocking means is the unlocking element. The unlocking element frees the syringe from the system after actuation. The leaf spring element brings the plunger into position, such that the spiral spring can move the storage element with the syringe body.

The unlocking element is actuated via the manually controlled grip face and the spring element.

BRIEF DESCRIPTION OF THE DRAWINGS

A detailed description follows, with reference to the attached drawings, wherein.

DETAILED DESCRIPTION

Figure 1:
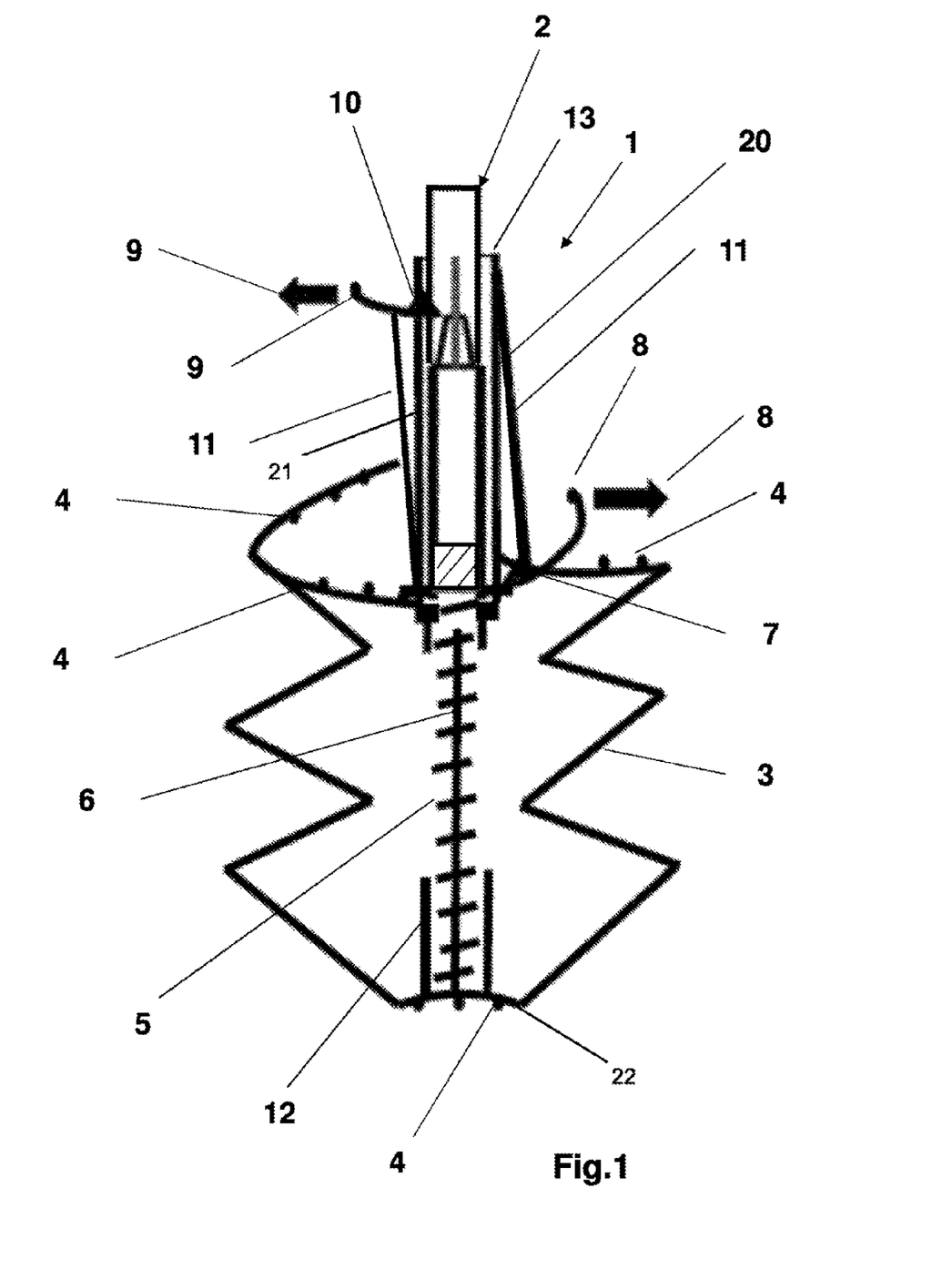
FIG. 1 is a cross section of a disposable syringe according to the invention.

Further advantages, features and details of the invention will become clear from the following description of preferred illustrative embodiments and by reference to the drawings, in which FIG. 1 shows a cross section of a disposable syringe 1 according to the invention composed of the discharge element 20 with a fitted storage element 2. A first locking means 8 and a second locking means 9 are also shown. The pretensioned spiral spring 5, which is integrally connected centrally on the plunger 6 to the leaf spring 3 with the integrated grip faces 4, shows the system prior to the injection. A spring guide 12 is also shown.

A spring guide 12 protrudes cylindrically from a leaf spring base 22 and serves to partially receive the spiral spring 5 and the plunger 6. At one end, the spiral spring 5 is integrally connected to the grip face 4 via the spring guide 12. The plunger 6 in turn is likewise connected to the grip face 4. The spiral spring 5 engages around the plunger 6. Through the compression of the leaf spring 3, the plunger 6 activates the storage element 2, such that a stopper 18 discharges the content of the storage element 2 via the injection needle 16, wherein the injection needle 16 comprises is at a first end of the syringe body 17, and the stopper 18 and an engagement flange 19 are present at a second end.

The first locking means 7 and a spring element 11 can also be seen, which are formed as a part of the discharge element 20.

Lastly, a puncture abutment face 13 can be seen in FIG. 1, which abuts against the skin during the injection.

Figure 2:
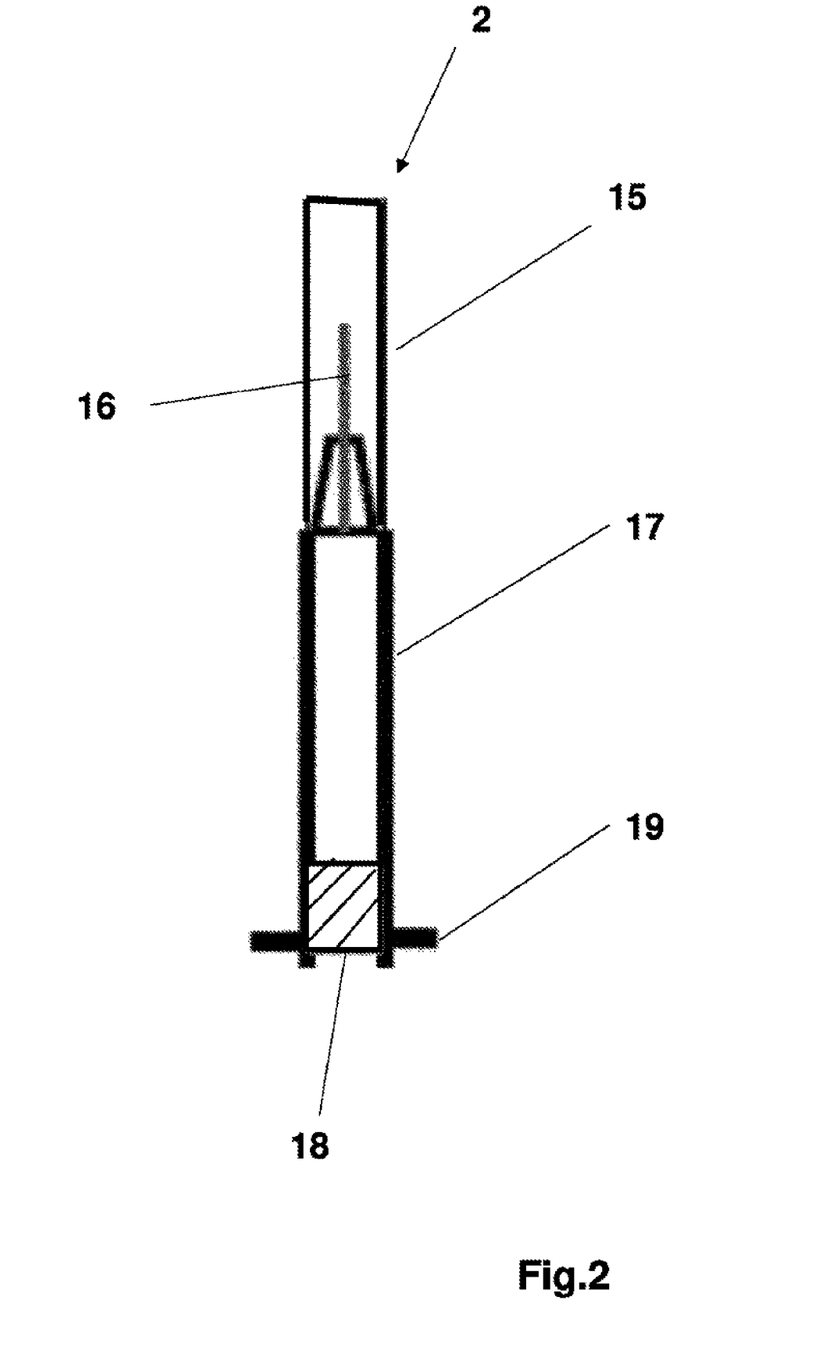
FIG. 2 is a cross section of a storage element according to the invention.

FIG. 2 shows the storage element 2 in cross section, with a protective cap 15 over the injection needle 16 on the syringe body 17, and the stopper 18 as movable base. The engagement flange 19 has the role of fixing the system in the discharge element 20.

Figure 3:
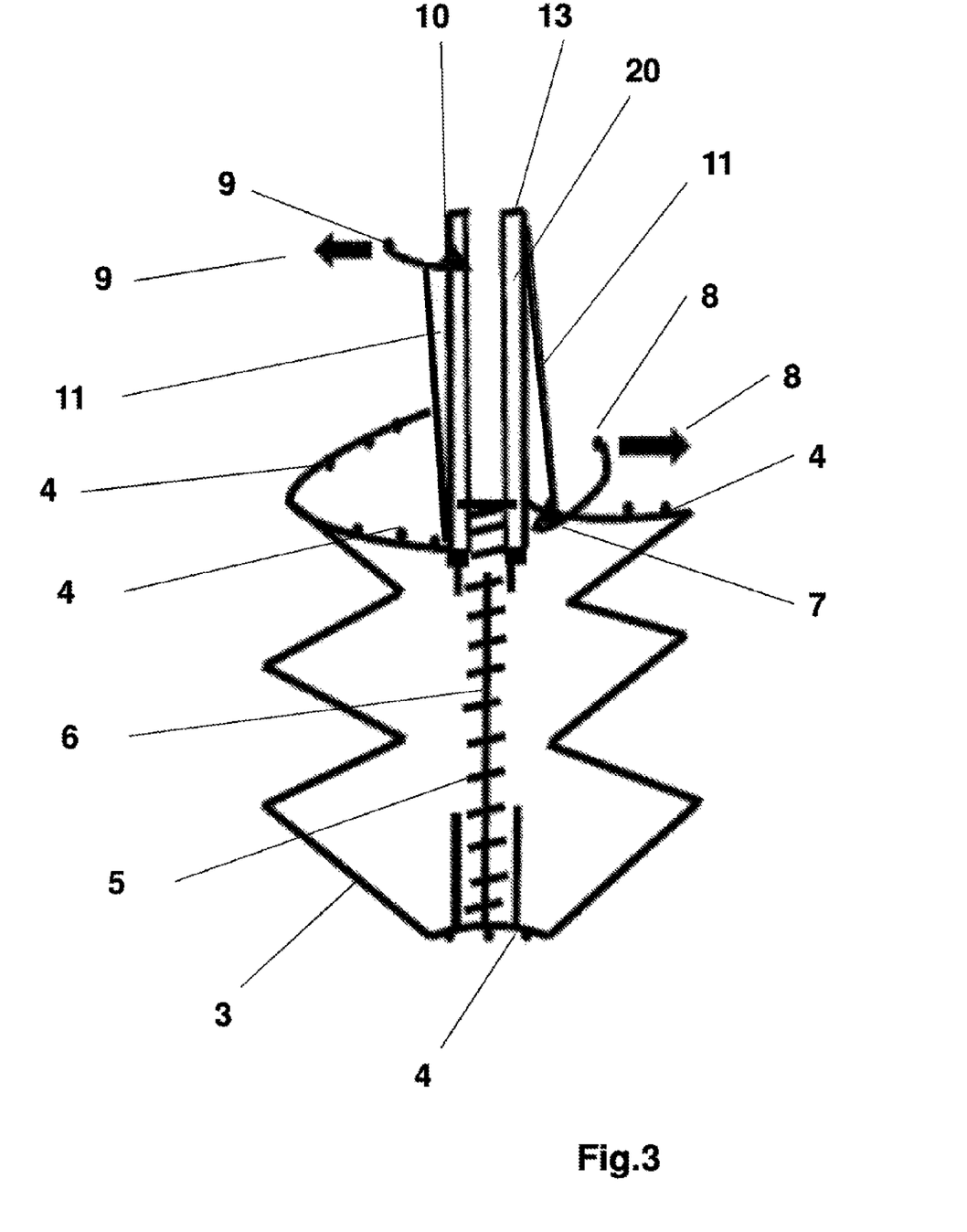
FIG. 3 is a cross section of a discharge element.

FIG. 3 shows a cross section through the discharge element 20 without the storage element 2. In the upper region, the second locking means 9 sits on the spring element 11. In the region of the grip face 4, the unlocking element 8 sits connected to the spring element 11. The grip faces 4 permit handling for self-medication or use by the physician. The doubled leaf spring system 3 brings the plunger 6 into position. The puncture abutment face 13 is embodied at the upper end of the system. Here, at the upper end means the end of the of the discharge element 20 lying opposite the leaf spring base 22. The puncture abutment face 13 is formed cylindrically and integrally onto the leaf spring element 3.

Figure 4:
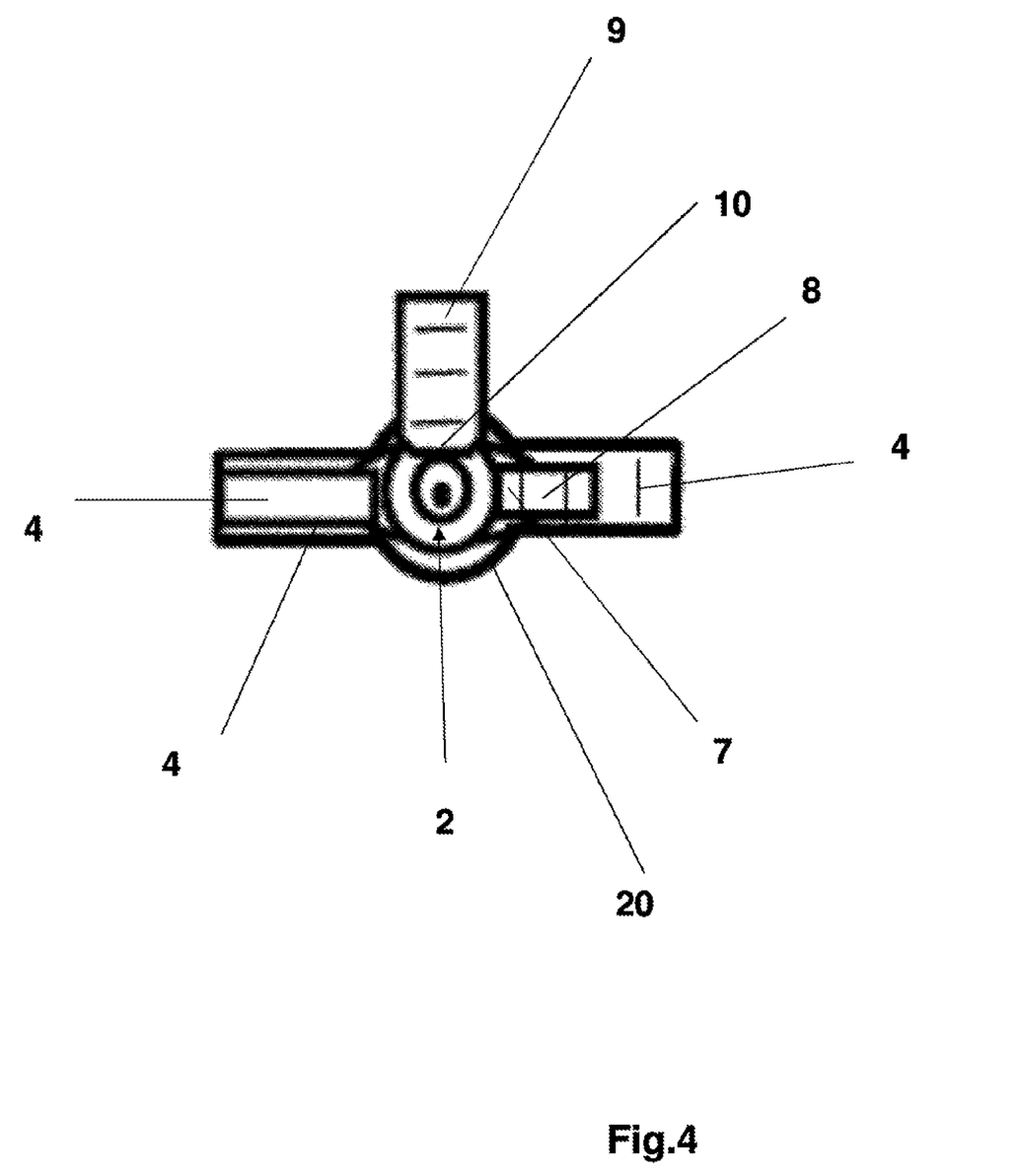
FIG. 4 is a plan view of the system according to the invention.

FIG. 4 shows the system in a plan view with the grip faces 4, the first locking means 7 with a locking cam 8, and the second locking means 9 with a further locking cam 10.

Figure 5:
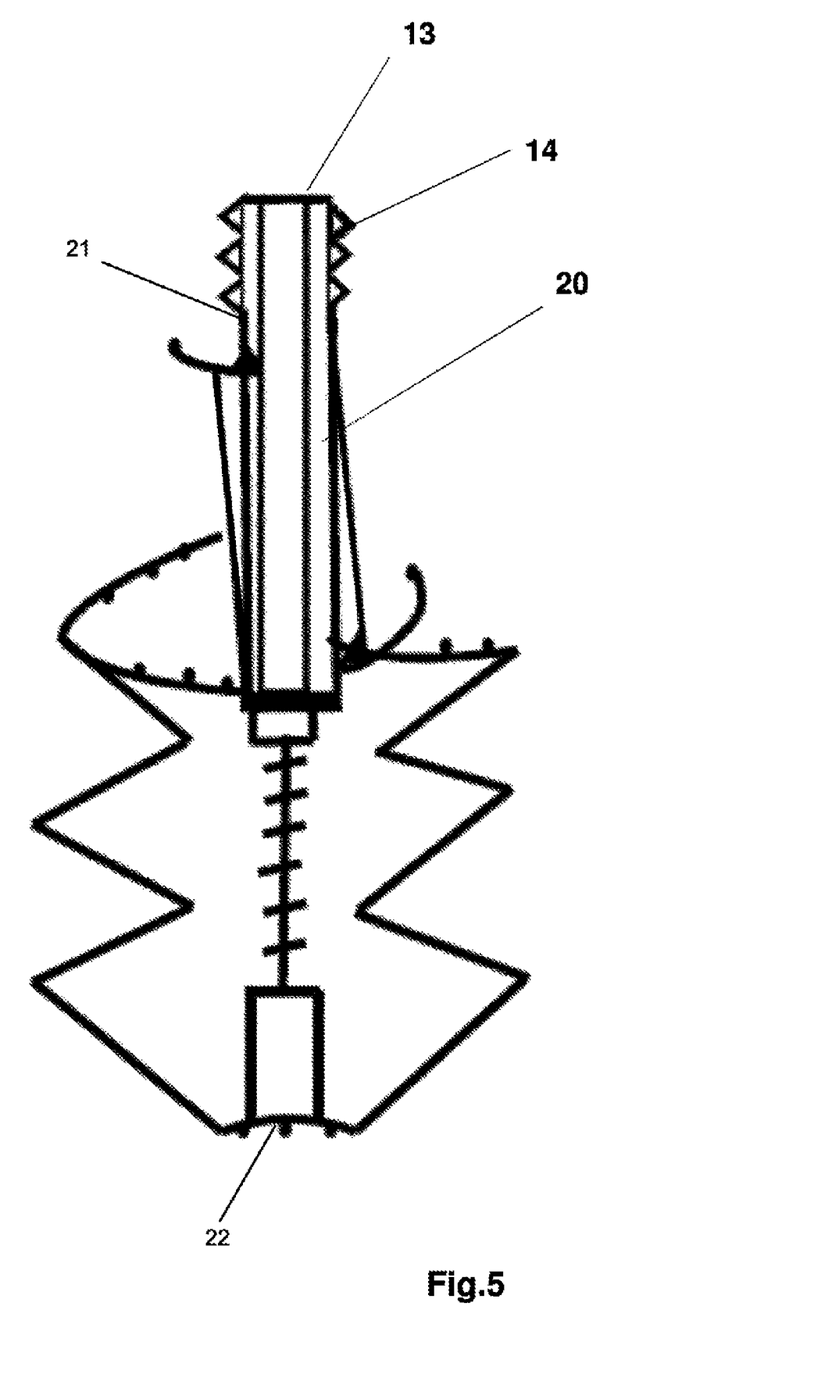
FIG. 5 shows an alternative embodiment of the invention with a bellows integrated into the discharge.

FIG. 5 shows a variant of the system with a bellows 14 integrated on the discharge element 20 for protecting the needle 16 in the storage element 2.

Figure 6:
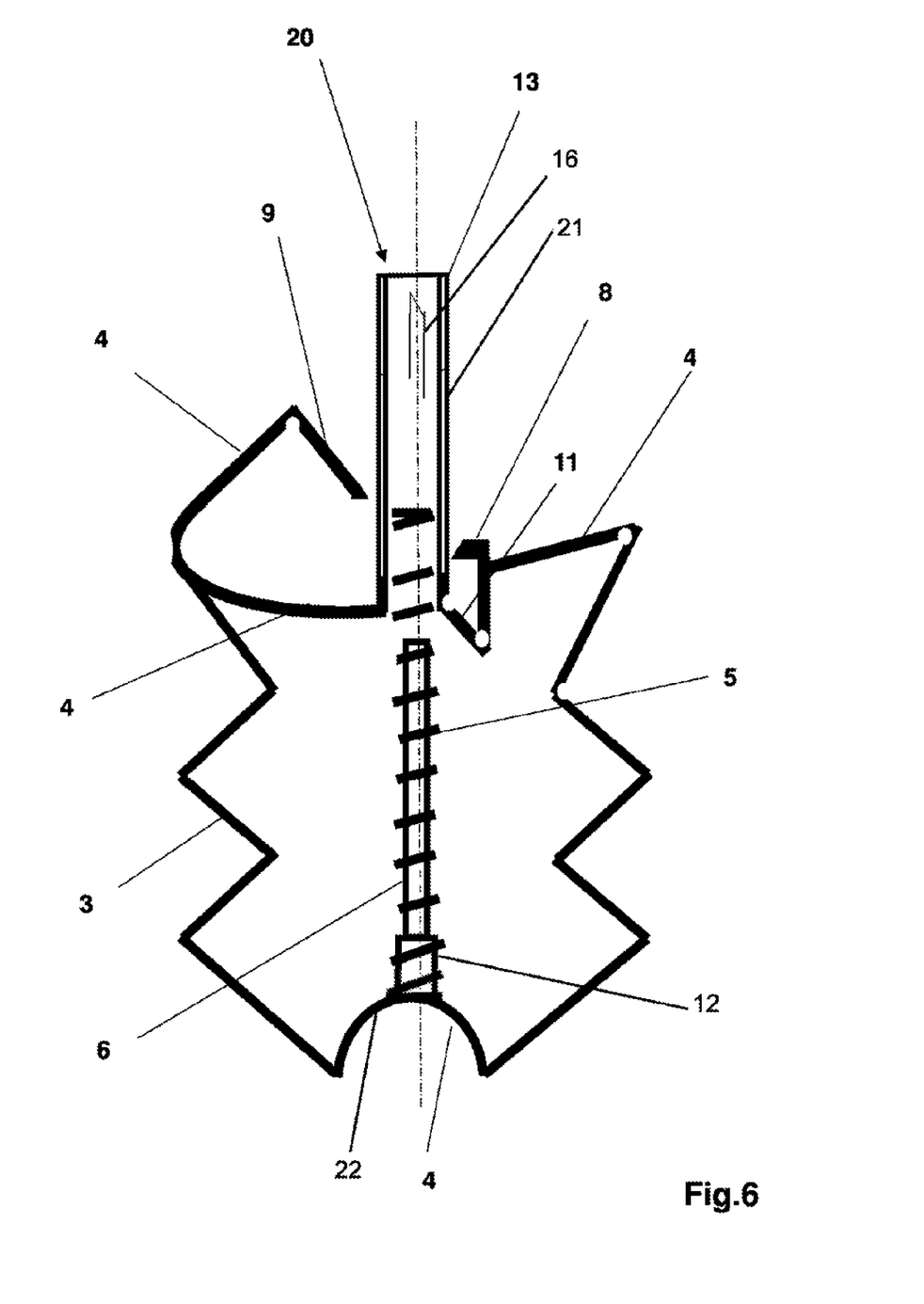
FIG. 6 is a cross section through the discharge element according to an unlocking variant of the invention.

FIG. 6 shows a cross section through the discharge element 20 with an unlocking variant. In the upper region, the unlocking element 9 sits with the grip variant designed for the physician and for self-medication. The vertical unlocking means 8 connected to the spring element 11 in the region of the grip face 4 is the first manual unlocking of the system for injection. The second unlocking via the unlocking element 9 frees the syringe from the system. The leaf spring element 3 brings the plunger 6 into position, such that the spiral spring 5 can move the storage element 2 with the syringe body 17.

Figure 7:
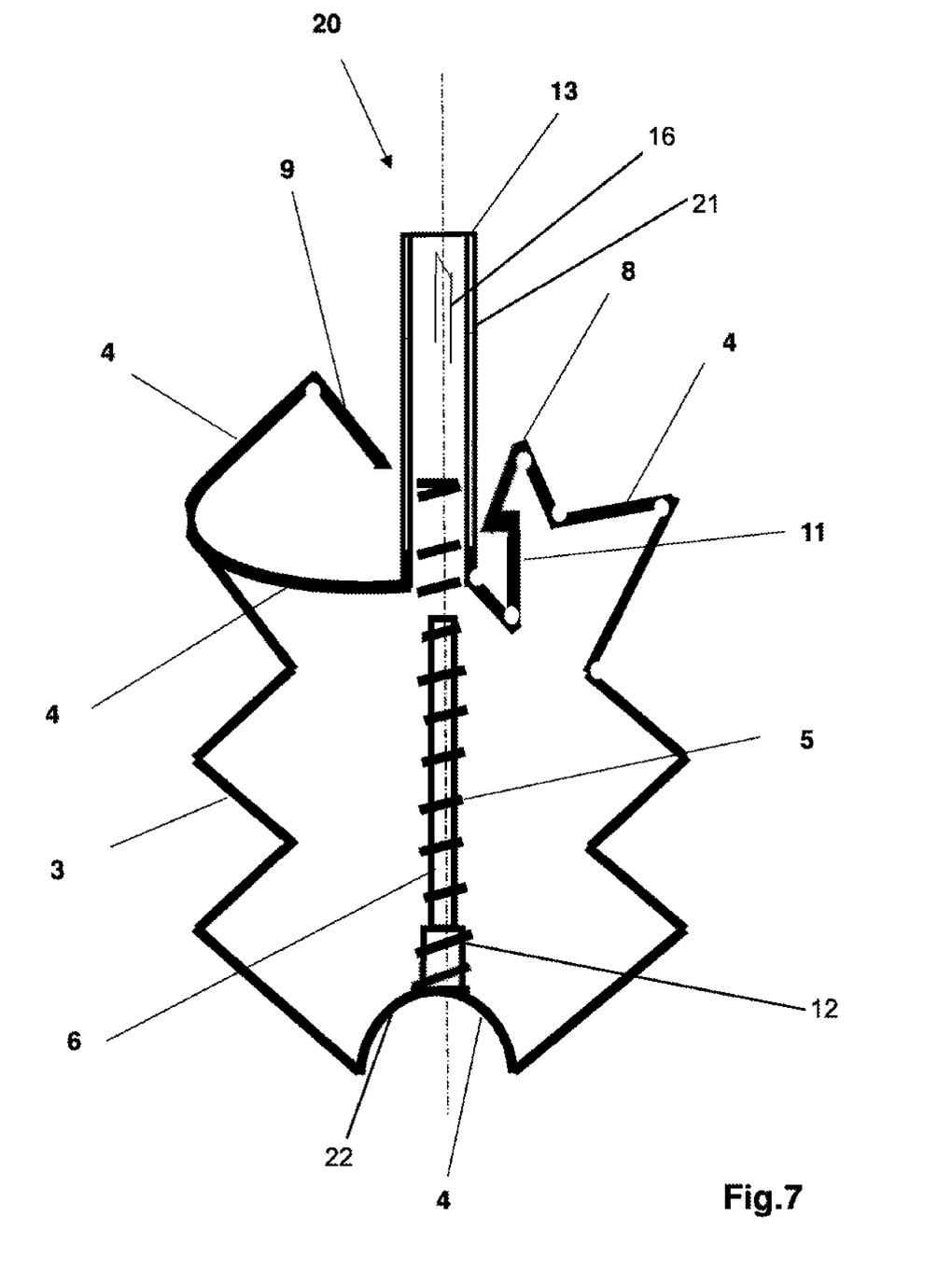
FIG. 7 illustrates an alternative embodiment of the vertical unlocking in a cross section through the discharge element.

FIG. 7 shows a variant of the vertical unlocking 8 in a cross section through the discharge element 20. The unlocking element 8 is actuated via the manually controlled grip face 4 and the spring element 11.

LIST OF REFERENCE SIGNS 1 syringe
2 storage element
3 leaf spring system
4 grip faces
5 spiral spring
6 plunger
7 first locking means
8 locking cam
9 second locking means
10 further locking cam
11 spring elements
12 spring guide
13 puncture abutment
14 bellows
15 protective cap
16 injection needle
17 syringe body
18 stopper
19 engagement flange
20 discharge element
21 discharge sleeve
22 leaf spring base

The invention claimed is:

1. A syringe having a discharge element (20) and having a storage element (2), wherein the discharge element (20) has a discharge sleeve (21) and a spring system (3), wherein the storage element (2) has a syringe body (17), and an injection needle (16) is formed at one end on the syringe body (17) and an engagement flange (19) is formed at the other end, wherein a movable stopper (18) is arranged in the syringe body (17), wherein the spring system (3) comprises a plunger (6) and a spiral spring (5) arranged around the plunger (6), wherein the plunger (6) and the spiral spring (5) can be pushed into the discharge sleeve (21), and the spiral spring (5) is arranged between a spring base (22), wherein the plunger (6) abuts against the stopper (18) and the spiral spring (5) abuts against a spiral spring stop (12) at the spring base (22), wherein the discharge sleeve (21) has a guide channel and the discharge sleeve (21) comprises a first locking means (7) and a second locking means (9), wherein the syringe body is moveable along the discharge sleeve between a first position wherein the engagement flange (19) of the syringe body is fixable and releasable at the first locking means (7), and a second position wherein the engagement flange (19) of the syringe body is fixable and releasable at the second locking means (9), wherein the discharge sleeve (21) has a puncture abutment face (13) at one end and the first locking means (7) is formed at the other end, wherein the puncture abutment face (13) comprises a receptacle, and wherein the puncture abutment face (13) comprises a bellows (14).

2. The syringe as claimed in claim 1, wherein the discharge sleeve (21) has a further guide channel, wherein a further engagement flange can be operatively connected to the further guide channel.

3. The syringe as claimed in claim 2, wherein the first locking means (7) locks and releases the engagement flange (19), and the second locking means locks and releases the further engagement flange.

4. The syringe as claimed in claim 1, wherein the stopper (18) is displaceable in the storage element (2) and sealed off.

5. The syringe as claimed in claim 1, wherein the first locking means (7) comprises a first spring element, wherein the first spring element is integrally connected to the spring system (3).

6. The syringe as claimed in claim 1, wherein the second locking means (19) comprises a second spring element, wherein the second spring element is integrally connected to the spring system (3).

7. The syringe as claimed in claim 1, wherein the bellows (14) is arranged on the receptacle.

8. The syringe as claimed in claim 1, wherein the spring system (3) is composed of the loaf spring base (22) and a ceiling region, wherein the ceiling region comprises the discharge sleeve (21), wherein the plunger (6) extends from the spring base (22) to the ceiling region and, between the spring base (22) and the ceiling region, a compression spring element is integrally formed with the spring base (22) and the ceiling region, wherein the compression spring element comprises a retention element.

* * * * *